US006716461B2

(12) United States Patent
Miwa et al.

(10) Patent No.: US 6,716,461 B2
(45) Date of Patent: Apr. 6, 2004

(54) METHOD FOR MODIFYING RAW MATERIAL MILK AND DAIRY PRODUCT PREPARED BY USING THE MODIFIED RAW MATERIAL MILK

(75) Inventors: Noriko Miwa, Kawasaki (JP); Yoshiyuki Kumazawa, Kawasaki (JP); Hiroyuki Nakagoshi, Kawasaki (JP); Shoji Sakaguchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/970,935

(22) Filed: Oct. 5, 2001

(65) Prior Publication Data

US 2002/0061358 A1 May 23, 2002

(30) Foreign Application Priority Data

Oct. 10, 2000 (JP) ........................................ 2000-309445

(51) Int. Cl.$^7$ ................................................. A23C 9/12
(52) U.S. Cl. ...................... 426/34; 426/42; 426/330.2; 426/580
(58) Field of Search ............................ 426/34, 36, 40, 426/42, 330.2, 580, 582

(56) References Cited

U.S. PATENT DOCUMENTS

| 5,670,192 A | 9/1997 | Budolfsen et al. |
| 5,681,598 A | 10/1997 | Kuraishi et al. |
| 5,736,356 A | 4/1998 | Sano et al. |
| 6,013,498 A | 1/2000 | Yokoyama et al. |
| 6,093,424 A | 7/2000 | Han et al. |
| 6,383,533 B1 | 5/2002 | Soeda et al. |

FOREIGN PATENT DOCUMENTS

| EP | 0 610 649 | 8/1994 |
| EP | 0 711 504 | 5/1996 |
| JP | 58-149645 | 9/1983 |
| JP | 05-268874 | 10/1993 |
| JP | 07-075569 | 3/1995 |
| JP | 07-134947 | 5/1995 |
| JP | 09-135664 | 5/1997 |
| JP | 11-000105 | 1/1999 |
| JP | 11-137254 | 5/1999 |
| WO | WO 93/22930 | 11/1993 |
| WO | WO 94/21129 | 9/1994 |
| WO | WO 96/22366 | 7/1996 |

OTHER PUBLICATIONS

Dickinson et al., AN 414308 FROSTI, abstracting Journal of Agriculture and Food Chemistry, 1996, 44(6), 1371–1377.*
F. Traore, et al., *J. Agric. Food Chem.*, vol. 39, pp. 1892–1896 (1991).
M. Faergemand, et al., *Food Hydrocolloids*, vol. 11, No. 1, pp. 19–25 (1997).
S. Lauber, et al., *Eur Food Res Technol*, vol. 210, pp. 305–309 (2000).
J.Y. Imm, et al., *Journal of Food Science*, vol. 65, No. 2, pp. 200–205, 2000.
S. Lauber, et al., *Eur Food Res Technol*, Art. 104/3011, pp. 305–309, 1999.
S.–T. Jiang, et al., *Journal of Food Science*, vol. 65, No. 2, pp. 241–245, 2000.
Von P. Chr. Lorenzen, et al., *Milchwirtschaftliche Forschungsberichte*, vol. 51(1), pp. 89–97, 1999.
K. Iwatsuki, et al., *Nippon Shokuhin Kagaku Kogaku Kaishi*, vol, 46, No. 9, pp, 535–542, 1999.
P. Chr. Lorenzen, et al., *Kiel. Milchwirtsch. Forschungsber*, vol. 49(3), pp. 221–227, 1997.
M. Faergemand, et al., *J. Agric. Food Chem*, vol. 45, pp. 2514–2519, 1997.
M. Faergemand, et al., *Food Hydrocolloids*, vol. 11, No. 1, pp. 19–25, 1997.
M. Faergemand, et al., *Food Hydrocolloids*, vol. 11, No. 3, pp. 287–292, 1997.
E. Dickinson, et al., *J. Agric. Food Chem.*, vol. 44, pp. 1371–1377, 1996.
F. Traore, et al., *J. Agric. Food Chem.*, vol. 40, pp. 399–402, 1992.
M. Nonaka, et al., *Journal of Food Science*, vol. 57, No. 5, pp. 1214–1218, 1992.
F. Traore, et al., *J. Agric. Food Chem.*, vol. 39, pp. 1892–1896, 1991.
R. Aboumahmoud, et al., *J Dairy Sci*, vol. 73, pp. 256–263, 1990.
N. Seki, et al., *Nippon Suisan Gakkaishi*, vol. 56(1), pp. 125–132, 1990.
N. Nio, et al., *Agric. Biol. Chem.*, vol. 50(4), pp. 851–855, 1986.
M. Griffin, et al., *Molecular and Cellular Biochemistry*, vol. 58, pp. 37–49, 1984.
K. Ikura, et al., *Agric. Biol. Chem.*, vol. 45(11), pp. 2587–2592, 1981.

* cited by examiner

*Primary Examiner*—Leslie Wong
(74) *Attorney, Agent, or Firm*—Oblon, Spivak, McClelland, Maier & Neustadt, P.C.

(57) ABSTRACT

Herein is disclosed a method for modifying raw material milk, wherein a reducing agent such as a thiol compound is added when transglutaminase is caused to act upon raw material milk for a dairy product, whereby the reactivity of the transglutaminase to the raw material milk such as raw cow milk, can be improved and the milk protein can, in turn, be modified effectively. From the thus-modified raw material milk can be produced dairy products such as yogurt, cheese and powdered milk improved in physical properties, mouthfeel or texture.

10 Claims, 4 Drawing Sheets

METHOD FOR MODIFYING RAW MATERIAL MILK AND DAIRY PRODUCT PREPARED BY USING THE MODIFIED RAW MATERIAL MILK

BACKGROUND OF THE INVENTION

1. [Technical Field of the Invention]

The present invention relates to a method for producing modified raw material milk for dairy products in which transglutaminase and a reducing agent are added to and caused to act on raw material milk for dairy products (i.e., milk as raw material for dairy products), such as raw milk or the like, whereby the milk proteins are cross-linked more effectively than before, in other words, a method for modifying milk as raw material for dairy products. By using the modified raw material milk produced according to the present invention, dairy products having improved physical properties, such as yogurt, cheese, powdered milk and the like having improved physical properties and provided with a favorable flavor and mouthfeel or texture, can be provided.

2. [Related Art]

In the production of dairy products, the value of the products depends largely on such physical properties as water-holding capacity, emulsion stability, viscosity, smoothness and the like. The manufacturers of dairy products have practiced a variety of devices to produce dairy products having further improved physical properties. For example, use of a variety of thickening polysaccharides for improving the mouthfeel and water-holding capacity of yogurt or ice cream has been widely known. Further, a variety of techniques such as use of a special lactic acid bacteria starter for reducing the separation of water from a yogurt (syneresis) (Japanese Patent Application Laid-Open No. 268874/1993), use of monoglycerides for obtaining a smooth processed cheese (Japanese Patent Application Laid-Open No. 105/1999), use of whey proteins for attaining the temperature stability of ice cream (Japanese Patent Application Laid-Open No. 135664/1997), and the like, have been reported.

Meanwhile, an attempt to improve the quality of a dairy product by using transglutaminase (Transglutaminase being abbreviated as "TG" hereinafter), which is an enzyme having the action of crosslinking proteins, has been reported. For example, it has been reported that the viscosity of a yogurt is increased by adding TG during the yogurt manufacturing process, whereby the separation of water from the yogurt (syneresis) is alleviated or reduced (Japanese Patent Application Laid-Open No. 197688/1994), that the yield of cheese curds is increased by using TG in the production process (Japanese Patent Application Laid-Open No. 173032/1996), and the like.

Such quality improvements with the use of TG have a variety of advantages from the industrial standpoint. Firstly, since even only an extremely small amount of TG is sufficient to exhibit the above effects, and at the same time, it acts directly on a food protein to exhibit the above effects, it has little adverse effect on mouthfeel. For example, when a thickening polysaccharide is added to a yogurt to improve its physical properties, even though such effects as an increase in viscosity, the prevention of separation of water from the yogurt or the like can be indeed attained, but the addition of the polysaccharide may not necessarily lead to an improvement in the overall quality of the yogurt due to the "gluey" mouthfeel of the thickening polysaccharide per se.

Secondly, in response to the customers' needs for taking in so-called "food additives" as little as possible, use of such an enzyme has a natural feel and provides a high added value to commercial dairy and the like products. Incidentally, a natural microorganism-derived TG has already been commercialized and widely used in various food processings.

The reports which have heretofore been made about the reactivity of TG to milk proteins are mainly those about the studies of whey proteins, particularly α-lactoalbumin and β-lactoglobulin which are the constituents of the whey protein, or a condensed whey protein. The whey protein is known as a protein to which TG has low reactivity due to its structure in which it has S—S bonds in the molecule (Fargemand et. al., J. Agric. Food. Chem. (1997) 45, 2,514–2,519, particularly p. 2,517, lines 41 to 53). For example, Traore and Meunier have reported that when Factor XIII (TG in blood) is introduced to act on the whey protein, crosslinking polymerization does not proceed in the absence of a reducing agent (J. Agric. Food Chem. (1992) 40, 399 to 402).

Further, Aboumahmoud and Savello (J. Dairy Sci. (1990) 73, 256 to 263) have reported that when α-lactoglobulin or β-lactoalbumin is crosslinked with the use of TG derived from guinea pig liver for the purpose of making a protein-based film, these whey proteins have to be preheated in the presence of a reducing agent at 85° C. for 15 minutes.

Fargemand et al. (Food Hydrocolloids, (1997) 11, 19 to 25) have made a report about the reaction between a whey protein and a calcium-independent TG and additionally reported that the TG has the effect of increasing crosslinked polymer in the presence of dithiothreitol (DTT) or cysteine and the effect of increasing the crosslinked polymer to some extent even under the alkaline conditions.

Casein, which is the main protein of milk proteins, is already known as a protein to which TG has a high reactivity (Fargemand et al., Food Hydrocolloids (1997) vol. 11, no. 3, pp. 287 to 292). For example, Nio et al. have reported the crosslinking polymerization of αS1-casein with a TG derived from guinea pig liver (Agrc. Biol. Chem. (1986), 50, 851 to 855), and Traore et al. have reported the crosslinking polymerization of purified caseins, particularly β-casein and κ-casein, with a Factor XIIIa from human.

As compared therewith, few studies have been made on the reactivity of TG to the casein in cow milk. Only Nonaka et al. have made a report about the study in which the crosslinking polymerization and gelation of reduced skimmed milk powder with TG were compared with those of a caseinate with TG. In the report, it is stated that the casein in the reduced skimmed milk powder is inferior to the caseinate in terms of reactivity (J. Food. Sci., (1992), 57(5), 1214 to 1218).

Not a few studies have been made on the physical properties of a gel or dairy product derived from the cow milk on which TG has been acted. For example, Fargemand et al. have reported the influence of crosslinking of the casein in skimmed milk powder by TG on acidic gelation (Food Hydrocolloids (1997) vol. 11, no. 3, pp. 287 to 292), Lauber et al. have reported the crosslinking of casein by TG and the gel strength of a yogurt (Eur. Food Res. Technol., (2000), 210(5), 305 to 309), and Imm et al. have reported the gelation and water-holding capacty of the skimmed milk powder treated with TG (J. Food Sci., (2000), 65(2), 200 to 205). In addition, Lorenzen et al. have reported the properties of a yogurt made from the cow milk treated with TG, the physical properties of a whipped cream, and the formability of curd with rennet (Kiel. Milchwirtsch. Forschungsber. (1997), 49(3), 221 to 227).

As has been described above, in the crosslinking reaction of cow milk proteins with TG, attempts to decrease the required amount of TG or reaction time by improving the reactivity of TG to a milk protein, particularly a casein, are not yet been made. The reasons for this are, for example, because when evaluation was made on the function or the like of a gel, milk used as a raw material had had sufficient reactivity to observe the effects caused by the addition of TG and that the need for further improving the reactivity of a casein which is an effective substrate for TG had not been recognized, and the like.

Meanwhile, a reducing agent such as glutathione or the like is used in an enzyme reaction for the purpose of stabilizing an enzyme or improving reactivity to the enzyme. As described above, an example thereof is to improve the reactivity of a whey protein by treating the whey protein with a reducing agent such as DTT to reduce S—S bonds.

As an example of improving the gel properties of food by using a reducing agent together with TG when TG was used on a food protein other than milk protein, it is known that the gel formability of frozen ground fish meat (surimi) can be improved by using TG, a protease inhibitor and a reducing agent in combination (S.-T. Jiang., et al., J. Food Sci. (2000), 65, 241 to 245). The reducing agent used in the above example is a sulfite. The reducing agent was, however, studied based on the amount which far exceeds the amount allowed to be added to food, and therefore has left a problem from the practical standpoint Further, it is believed to be desirable to contain a milk protein and a thiol group-containing compound for modifying a food protein using TG and an oxidoreductase (Japanese Patent Application Laid-Open No. 161849/1999). In this case, the thiol group-containing compound only serves as a substrate for the oxidoreductase and is not an essential element. In addition, even if this stabilizes and retains the activity of TG, the effect of improving the reactivity of the food protein to TG has not been mentioned.

Although it has been already described above that use of TG in dairy products has a number of advantages, not many commodity products in which TG has been actually used are on the current market. The reasons for this are thought to be because the expected effects are not obtained in the actual production of dairy products using raw milk or because the actually obtained effects are not valuable from the industrial standpoint. In other words, even if some effects can be obtained by the addition of TG in the actual production of dairy products using raw milk, the effects are not so significant to be considered valuable from the industrial standpoint.

Under these circumstances, the present inventors have made intensive studies on the reactivities of raw milk and a variety of milks as raw material using raw milk to TG and methods of treating these milks with TG. As a result, they have found that milks as raw material having a low heat history such as raw milk, have a low reactivity to TG.

The present inventors have found that the milk is first preheated to improve the reactivity of the milk to TG, so that the crosslinking reaction of the raw milk by TG can be promoted, to solve such a problem.

For example, it has been confirmed that cow milk sterilized at a low temperature (sterilized at 63° C. for 30 minutes) and cow milk sterilized at an ultra high temperature (sterilized at 130° C. for 2 to 3 seconds) have different reactivity to TG, i.e., the latter has a higher reactivity to TG than the former. Further, it has been confirmed that when the former is heat-treated (heated to 90° C.), the reactivity to TG is significantly improved.

Lorenzen et al. have also reported preheating raw material milk (at 95° C. for 2 seconds) before the reaction with TG in the production of a yogurt using TG (Kieler Milchwirtschaftliche Forschungsberichte, (1999), 51(1): 89 to 97).

However, although preheating of the milk is simple and easy, a preheating step must be provided separately from the reaction with TG. This affects the production process of dairy products and also requires thermal energy and time. Further, since the denaturation of a milk protein by heat treatment is promoted, a loss of the flavor of raw milk and an adverse effect on the mouthfeel of a dairy product by heating are concerned. In addition, there is also the problem that preheating cannot be applied to dairy products such as cheese to which excessive heat treatment is undesirable.

SUMMARY OF THE INVENTION

[Problem to be Solved by the Invention]

It is an object of the present invention to solve the above problems and provide a method for producing a dairy product having improved physical properties by improving the reactivity of TG to raw material milk such as raw milk.

[Means for Solving the Problems]

The present inventors have made intensive studies to find a method in which the effects caused by use of TG can be obtained more effectively without preheating raw material milk having a low reactivity to TG even when TG is used (added) in a small amount and the reaction time is short. As a result, they have obtained the technical findings that the reactivity of TG to the raw material milk can be significantly improved by adding a reducing agent and TG to the raw material milk and allowing the mixture to react.

As a result of further studies, the effect of improving the reactivity has been observed when the amount in terms of concentration, of the reducing agent to be added to the raw material milk, for example, in the case of reduced glutathione, is at least $7 \times 10^{-5}$ g per 1 gram of the non-fat milk solid. This amount corresponds to 0.0006% by weight of the raw material milk (non-fat milk solid: 8.4%). Further, the present inventors have also made studies on a yeast extract containing glutathione in high concentration from the viewpoints of its usability for food, cost effectiveness, functionality and stability and have observed the effect of improving the reactivity when the yeast extract is added in an amount of at least 0.007% based on the raw material milk. The effect of this concentration on the taste of food is negligible, and this has verified that the present invention is a technology with extremely high practicality in that it can be practiced by using a natural substance.

The method of the present invention for producing modified raw material milk comprising using TG and a reducing agent in combination. The two materials may be added to raw material milk simultaneously, or one of them may be added prior to the other. However, it is preferable to add them and allow them to react simultaneously or treat with TG after the addition of the reducing agent.

That is, the present invention relates to modified raw material milk obtained by adding practical amounts of a reducing agent and TG to raw material milk and allowing them to react to crosslink the milk proteins contained in the raw material milk more efficiently, and a novel production method capable of improving the physical properties of a dairy product produced by using the modified raw material milk.

DETAILED DESCRIPTION OF THE INVENTION

Figure 1:
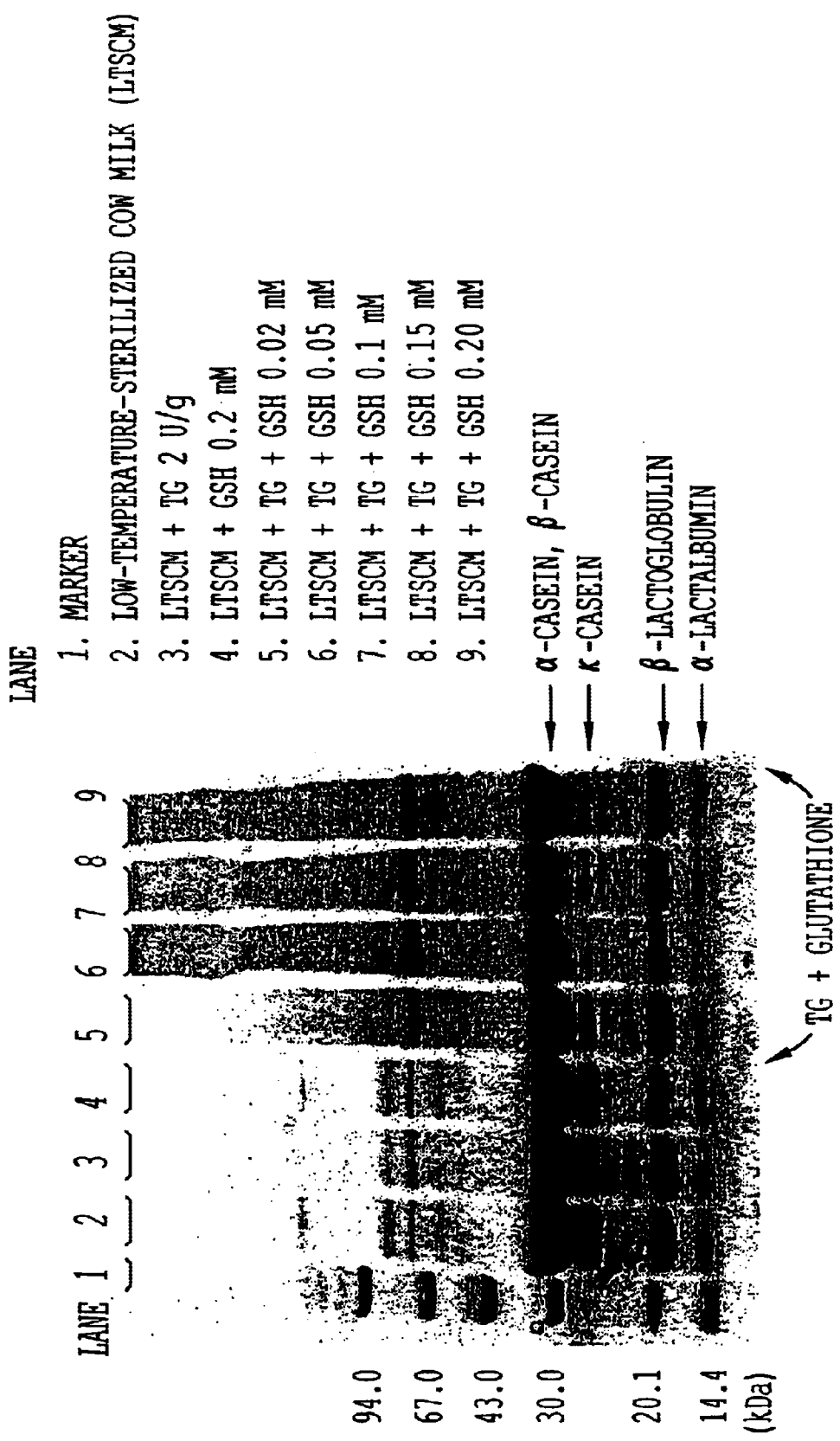
FIG. 1 shows a sodium dodecyl sulfate(SDS)-polyacrylamide gel electrophoresis pattern illustrating an improvement in the reactivity of raw material milk to TG by the addition of reduced glutathione (Example 1).

The present invention will be described in more detail hereinafter.

The raw material milk to be used according to the present invention is obtained from such animals as cows, goats and the like, and exemplified by raw milk, skimmed milk, partially skimmed milk or processed milks thereof. The "raw milk" is so-called "unprocessed milk" which is milk unprocessed after milked. The "skimmed milk" is obtained by removing almost all oils and fats from raw milk, and the "partially skimmed milk" is obtained by removing some oils and fats from raw milk.

The "processing" primarily refers to heat sterilization for making raw milk drinkable. Commercial cow milk is heat-sterilized milk. Commercial cow milk refers to the milk from cows which is sold to be drunk as it is, and has been heat-sterilized at temperatures from 62 to 65° C. for 30 minutes or heat-sterilized by a method having a similar sterilization effect.

In general, as an index or measure of this sterilization effect, that is, the degree of heating, a physicochemical property susceptible to the influence of heating such as the concentration of lactoferrin or lactulose, rennetability, the degree of denaturation of whey proteins, or the like, is used (Iwafu et al., "Japan Food Science and Engineering Journal", Vol. 46, No. 8 (1999), pp. 536 to 542).

For example, when the degree of denaturation of whey proteins is used as the index or the measure, raw cow milk containing denatured whey proteins at a concentration of 0 to 70% therein is preferable according to the present invention.

Cow milk sterilized at a low temperature (sterilized at 62 to 65° C. for 30 minutes) and cow milk sterilized at a high temperature for a short time (sterilized at 75° C. for 15 seconds) have a denaturation degree of whey proteins of about 10 to 12% (Iwafu et al., "Japan Food Science and Engineering Journal", Vol. 46, No. 8 (1999), p. 537). Thefore, these heat-sterilized cow milks are included in the raw material milks that can be used according to the method of the present invention.

The denaturation degree (%) of whey proteins can be calculated from the following calculating formual (Iwafu et al., "Japan Food Science and Engineering Journal", Vol. 46, No. 8 (1999), p. 536).
Degree of denaturation (%)=((absorbance of raw milk–absorbance of sterilized milk)/absorbance of raw milk)×100

Further, the denaturation degree of whey proteins can be measured by the following method (Iwafu et al., "Japan Food Science and Engineering Journal", Vol. 46, No. 8 (1999), p. 536). That is, after 22 g of sample has been kept at 37° C. for 30 minutes, 8 g of salt is added thereto. The resulting mixture is filtered, and a 1 ml portion of the filtrate is added with 10 ml of acidic saturated sodium chloride solution (prepared by adding 4 ml of glacial acetic acid to 1 liter of saturated saline solution). The absorbance of the resulting mixture is measured at 420 nm by using a spectrophotometer (disposable, optical path length: 10 mm, at room temperature).

Furthermore, processings other than heat sterilization include homogenization, mixing, demineralization, (membrane) separation and the like.

A casein-containing solution obtained from the above raw material milks by carrying out such treatments as centrifugation or the like is also included in the raw material milks that can be used according to the present invention.

Illustrative examples of the reducing agent to be used according to the present invention include thiol compounds such as glutathione, cysteine and γ-glutamylcysteine; yeast extracts containing at least one of them in high concentrations; thiosulfuric acid, sulfurous acid, ascorbic acid, erythorbic acid and salts thereof which are allowed to be used as food additives; and tocopherols. Preparations containing at least one of them are also included in the above reducing agent. The reducing agent to be used according to the present invention is not limited to those listed above as long as it is the one having a reducing effect.

The reducing agent can be added/used in an amount of 1 ×$10^{-5}$ to 1×$10^{-1}$ g per 1 gram of non-fat milk solid. For example, in the case of raw material milk having about 8 to 10% of non-fat milk solid, the reducing agent can be added in an amount of 0.0001 to 1.0% by weight based on the raw material milk. The effect of improving the reactivity is difficult to obtain when the amount of the reducing agent is smaller than the above range. On the other hand, when the amount of the reducing agent is too large, the addition of the reducing agent adversely affects the taste of food. In addition, depending on the type of the reducing agent, the effect of improving the reactivity remains the same once the amount of the reducing agent is increased to a certain amount, and increasing the amount of the reducing agent thereafter has no effect on the effect of improving the reactivity.

The reducing agent may be added to raw material milk anytime irrespective of when TG is added. This is because the effect of improving the reactivity by the addition of the reducing agent is the same when the reducing agent is added before or after the addition of TG or concurrently with TG. However, when the reducing agent is added after the addition of TG, the reactivity of raw material milk to TG remains low until TG is added to the raw material milk, and the reactivity starts to increase once the reducing agent is added. Therefore, the substantial acceleration of the reaction starts upon or after the addition of the reducing agent. From the practical standpoint, the reducing agent is desirably added concurrently with TG or before the addition of TG.

The TG to be used according to the present invention is an enzyme which catalyzes the acyl group transfer reaction which acyl group is present in the y-carboxyamide group of a glutamine residue in a protein or peptide chain. When this TG acts upon the s-amino group of a lysine residue as an acyl acceptor in a protein, ε-(y-glutamyl)-lysine bonds are formed in and between the molecules of the protein or intramolecularly and intermolecularly. By these crosslinks, strong networks are formed among the molecules of a milk protein in raw material milk, whereby modified raw material milk having such properties as high gel formability, high viscosity and high water-holding capacty is produced, and, in turn, a dairy product having improved physical properties can be produced by using the modified raw material milk. TG which is the enzyme to be used according to the present invention can be any TG as long as it has transglutaminase activity, and known TGs can be used.

TGs can be classified into calcium-independent TG and calcium-dependent one, and both types of TGs can be used according to the present invention. Illustrative examples of the former include those derived from microorganisms such as TG derived from Actinomycetes (refer to Japanese Patent No. 2,572,716), TG derived from bacillus subtilis (refer to Japanese Patent Application Laid-Open No. 137254/1999), and the like. Illustrative examples of the latter include TG derived from a guinea pig's liver (refer to Japanese Patent No. 1,689,614), TG derived from microorganisms such as Oomycetes and the like (refer to WO96/22366), TG derived from animal blood such as bovine blood, swine blood, and the like, TG derived from fishes such as salmon and sea bream (N. Seki et al., Nippon Suisan Gakkaishi (1990) 56, 125 to 132), and TG derived from oysters (U.S. Pat. No. 5,736,356), and the like.

In addition, those produced by gene recombination and the like can also be used (refer to Japanese Patent Application Laid-Open No. 75876/1999, for example). Any TG can be used according to the present invention and the TG is not limited to the particular source or production method. However, from the viewpoints of functionality and ease of use in food applications, calcium-independent TG is preferable. For example, the actinomycetes-derived TG (refer to Japanese Patent No. 2,572,716) satisfies all the conditions and can be said to be the most preferable TG at the present time, out of the above microorganism-derived TGs.

The activity unit of TG to be used according to the present invention is measured and defined as follows. That is, a reaction is carried out using benzyloxycarbonyl-L-glutaminylglycine and hydroxylamine as substrates, the produced hydroxamic acid is converted into an iron complex in the presence of trichloroacetic acid, and the amount of the iron complex is measured at an absorbance of 525 nm. The amount of the enzyme which produces 1 $\mu$mol of hydroxamic acid per 1 minute is defined as 1 activity unit of TG. The details of this measuring method (so-called "hydroxamate method") are just as have already been reported (refer to Japanese Patent No. 2,572,716, for example).

As has already been described above, it is known that TGs have a variety of origins. Depending on the origins, some TGs have the substrate specificity which inhibits defining the activity by the above hydroxamate method. In that case, the unit may be defined by a different method. Regardless of which activity-measuring method is used to define the unit, the amount of the TG is included within the range of the amount of TG which can be added according to the present invention as long as the first-mentioned amount is substantially the amount which exhibits what is called "the effect of improving the physical properties of a dairy product" according to the present invention.

TG can be added in an amount of 0.001 to 20 units, preferably 0.01 to 10 units, per 1 gram of milk proteins. When the amount is less than 0.001 units, the expected effect cannot be obtained, while when the amount is more than 20 units, an excessive reaction occurs. This is not only uneconomical but also makes the expected effect difficult to obtain.

The reaction temperature of TG can be generally about 0 to 60° C., and the reaction time can be about 5 minutes to about 48 hours. However, TG is preferably allowed to react at about 5 to 50° C. for about 30 minutes to about 24 hours.

The degree of crosslinking of milk proteins with the use of TG, in other words, the degree of modification of milk with the use of TG, can be appropriately adjusted by such reaction conditions as the amount, reaction time, reaction temperature and the like, concerning TG, depending on the physical properties of the desired dairy product. The degree of crosslinking of milk proteins can be examined by a quantitative method and a qualitative method. Illustrative examples of the quantitative method include the analysis of the quantity of the $\epsilon(\gamma$-glutamyl) lysine bonds, i.e., G-L bonds, in proteins by liquid chromatography (Griffin and Wilson, Molecular and Cellular Biochemistry (1984), 58, 37 to 49) and the measurement of the amount of ammonia produced by the crosslinking reaction (Ikura et al., Agricultural and Biological Chemistry, (1980), 45, 2587 to 2592). Illustrative examples of the qualitative method include a method of examining the degree of crosslinking and the molecular weight by electrophoresis (Traore and Meunier, Journal of Agricultural and Food Chemistry, (1991), 39, 1892 to 1890).

To terminate the reaction, the heat sterilization conditions which are generally used in the production of dairy products are used as they are, and such conditions should not be particularly limited. As a matter of course, the effect of the present invention can still be obtained without using such a heat sterilization process.

The thus-obtained modified raw material milk per se is also included in the dairy products obtained by the production method of the present invention (in broad sense).

According to the present invention, as has been described above, a sufficient reactivity-improving effect can be realized with the use of TG and a reducing agent without preincubation. Thus, the method of the present invention is excellent in convenience and practicality in that it does not require the time, process steps and energy such as heat for improving the reactivity of TG. Further, for example, when an enzyme preparation containing TG and a reducing agent is used, the method of the present invention can be carried out simply by adding the preparation and taking a reaction step.

In addition, although a description has been given to the examples in which TG and a reducing agent are used in food, the reducing agent which has been used according to conventional knowledge lacks practicality in that it cannot be used in food depending on the type of the reducing agent or that even if it can be used as a food additive, it is used in an amount exceeding the amount permitted to be used.

The present invention is excellent in that the required amount of a reducing agent is at a realistic level where the reducing agent can be used in food. For example, when a yeast extract containing glutathione in high concentration or an ascorbate is used according to the present invention, they can be used in such amount that they hardly affect the taste of foods such as milk and dairy food.

EXAMPLES

The present invention will be described in detail with reference to Examples hereinafter.

Example 1

Reduced glutathione was added to 5 ml of low-temperature-sterilized cow milk (kept at 63° C. for 30 minutes to be sterilized; non-fat milk solid: 8.4%; milk protein: 3.1%; milk fat: 3.6%) in such amount that the content of the reduced glutathione in the milk would be 0 to 0.2 mM, and together with the reducing agent, an enzyme preparation of TG("ACTIVA" TG, specific activity: 1,000 units/gram of the preparation, product of AJINOMOTO CO., INC.) was added in an amount of 2 units per 1 gram of milk proteins. The reaction was carried out by keeping the resulting mixture at 40° C. for 3 hours. The degree of crosslinking of the proteins was examined by SDS-polyacrylamide gel electrophoresis. The detection of the proteins was carried out by immersing a gel containing migrated proteins in a solution containing dye (Coomassie brilliant blue) which specifically bonds to the proteins caused to migrate into the gel by electrophoresis and then destaining the gel.

The result of the migration pattern with 0 to 0.2 mM of reduced glutathione is shown in FIG. 1.

Figure 2:
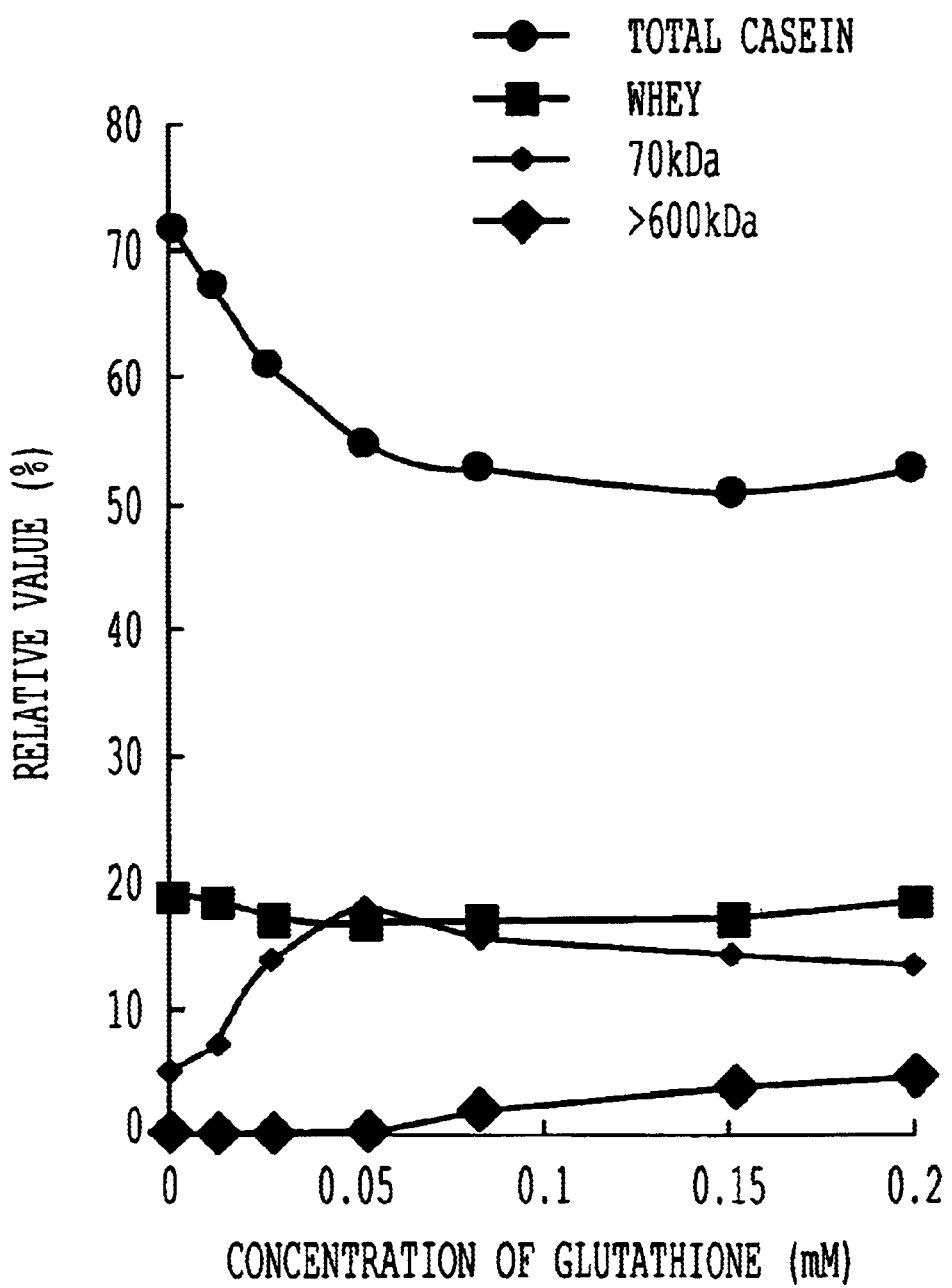
FIG. 2 shows the amount of reduced glutathione added and a change in the crosslinked polymer (Example 1).

The result of conducting the quantitative analysis of the band by a densitometer based on the above result is shown in FIG. 2.

Referring to FIG. 2, the total band amount (relative value) of caseins ($\alpha$-casein, $\beta$-casein and $\kappa$-casein) decreased as the reduced glutathione was added in increased amounts. Meanwhile, the proportion of molecules which were crosslinking polymerized by TGs of 70 kilodaltons and not smaller than 600 kilodaltons was increased. As for a whey protein, a decrease in the band due to the crosslinking by TG was observed but the decrease was small.

The acceleration of crosslinking polymerization of the caseins by the reduced glutathione was observed when the concentration of the reduced glutathione was about 0.02 mM or higher. This concentration was $7 \times 10^{-5}$ g per 1 gram of non-fat milk solid, that is, 0.0006% based on the weight of the raw material milk.

Example 2

In the same manner as in Example 1, sodium ascorbate was added to 5 ml of low-temperature-sterilized cow milk in such amount that the concentration of the sodium ascorbate in the milk would be 0 to 1.0%, and together with the sodium ascorbate, an enzyme preparation of TG ("ACTIVA" TG, specific activity: 1,000 units/gram of the preparation, product of AJINOMOTO CO., INC.) was added in an amount of 2 units per 1 gram of the milk proteins. The reaction conditions and the subsequent electrophoresis were the same as described above. The result of the electrophoresis is shown in FIG. 3.

Figure 3:
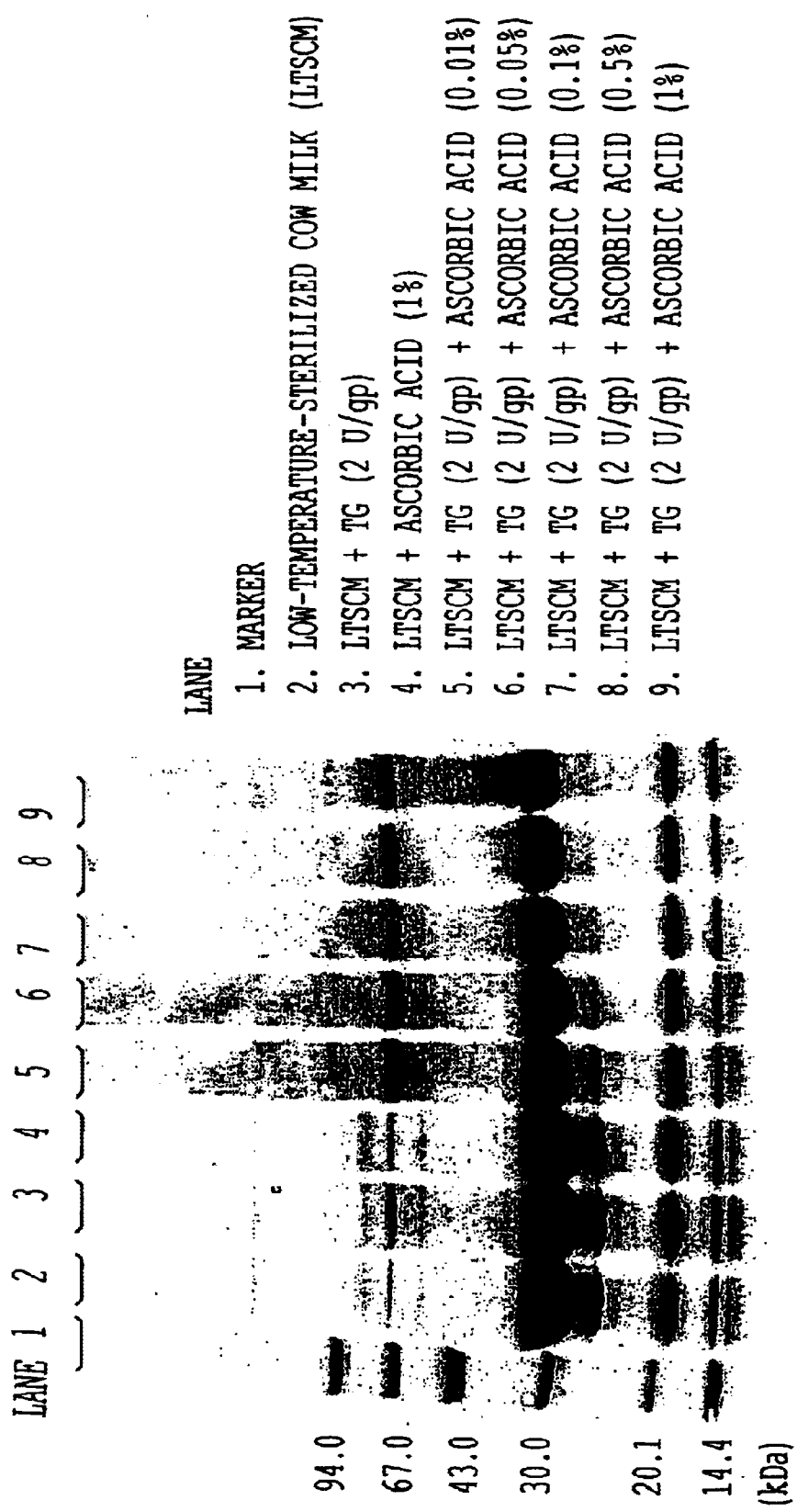
FIG. 3 shows an SDS-polyacrylamide gel electrophoresis pattern illustrating an improvement in the reactivity of raw material milk to TG by the addition of sodium ascorbate (Example 2).

Referring to FIG. 3, the amount of the sodium ascorbate required to obtain a maximum reactivity-improving effect was larger than that of the reduced glutathione of Example 1. It was understood from this that the effect of improving the reactivity varies depending on reducing agents.

Although not shown, the same test was conducted on cysteine, $\gamma$-glutamylcysteine, sodium bisulfite, sodium ascorbate and erythorbic acid, and the same results were observed. Above all, thiol compounds such as reduced glutathione, $\gamma$-glutamylcysteine, and the like exhibited a great effect. Further, a yeast extract ("AROMILD U", product of KOJIN Co., Ltd.) containing glutathione in a concentration of 8%, exhibited the same effect as the reduced glutathione did.

The above-described facts on which the present invention is based are novel findings which has never been found before, for, referring to FIG. 2 showing the result of conducting the quantitative analysis of the band by a densitometer, it can be determined that the mechanism of the effect of improving the reactivity of raw material milk to TG according to the present invention is ascribable to an improvement in the reactivity of a casein rather than a whey protein. Therefore, this cannot be explained by the aforementioned conventional knowledge, i.e., an improvement in the reactivity of a whey protein to TG by a reducing agent.

Further, the required amount of a reducing agent according to the present invention is extremely small as the amount required for improving the reactivity of a whey protein to TG.

Although it has been described above that an improvement in the reactivity of a whey protein to TG with a reducing agent is caused by the cleavage of the S—S bond in a molecule, it is known that this varies depending on the time spent for the treatment with the reducing agent. That is, the improvement in the reactivity of a whey protein to TG increases in proportion to the time spent for the incubation of the whey protein with the reducing agent. Therefore, when the reducing agent and TG are added simultaneously without preincubation, the effect of improving the reactivity of the whey protein to TG is small.

However, in the case of the present invention, there is little difference in the effect of improving the reactivity between the case where a reducing agent and TG are added to raw material milk simultaneously and the case where TG is added after the raw material milk and the reducing agent have been incubated. From the foregoing as well, it can be assumed that the possibility that an improvement in the reactivity of a whey protein to TG by reduction treatment contributes, is small.

As has been described above, one of the roles of a reducing agent according to an enzyme reaction is the activation of enzymes. However, the reducing agent according to the present invention does not play this role. This is because, although not shown, it has been recognized that the activity of TG is hardly affected by the addition of the reducing agent in the absence of milk proteins. Even if the reducing agent exhibits the effect of activating TG or preventing an decrease in the activity of TG in raw material milk, it is hardly conceivable that it has the effect of changing the reaction amount drastically as according to the present invention.

Therefore, can be is assumed that a change in the structure of a casein, particularly, a casein micelle greatly contributes to an improvement in the reactivity of raw material milk to TG by the treatment with a reducing agent. That is, although the casein is basically known as a protein having a high reactivity to TG, it exhibits a low reactivity in raw material milk. It can be assumed that this has something to do with the state of casein, i.e., a difference in reactivity between a purified casein and a casein micelle.

As regards the reactivity of each constituent of the casein, that is, the reactivities of $\alpha$-casein, $\beta$-casein and $\kappa$-casein, it is said that $\beta$-casein has the highest reactivity, and $\alpha$-casein and $\kappa$-casein have lower reactivity than $\beta$-casein. It is known that the surface of the casein micelle is covered with $\kappa$-casein, and it can be assumed that this causes the low reactivity of the whole raw milk material to TG. It can be assumed that the reducing agent changes, according to the present invention, the structure of the casein micelle, and promotes the separation of $\beta$-casein having high reactivity from the micelle to improve the reactivity.

According to a number of experiments performed by the present inventors, the technology of the present invention exhibited a more significant effect in improving the physical properties of a yogurt. In the production of the yogurt, an example of the present invention will be described below.

Example 3

Production of Yogurt

An enzyme preparation of TG ("ACTIVA" TG, specific activity: 1,000 U/g of the preparation, product of AJINOMOTO CO., INC.) was added to 300 ml of low-temperature-sterilized cow milk (kept at 63° C. for 30 minutes to be sterilized; non-fat milk solid: 8.4%; milk protein: 3.1%; milk fat: 3.6%) in the proportion of 2 units per 1 gram of the milk proteins, and at the same time, "AROMILD U" (product of KOJIN Co., Ltd., yeast extract containing 8% of glutathione) was added in the proportion of 0.02% based on the raw material milk. While maintained at 40° C., the mixture was stirred and allowed to react for 1, 2 or 4 hours (Test sections a, b and c, all of which are products according to the present invention). To terminate the reaction, the mixture was heated to 90° C. and then immediately cooled to 47° C.

To each of the thus-obtained modified raw material milks, a commercial lactic acid bacteria starter "Yo Flex YC-370" (product of Chrischan Hansen's Laboratories) was added in the proportion of 0.0063% based on the raw material milk. After the resulting milks were charged into containers, they were respectively fermented at 44° C. until the pH reached 4.5, whereby yogurts were prepared.

For comparison, yogurts were prepared similarly from the low-temperature-sterilized cow milk added neither with TG nor "AROMILD U" (Control section 1), the low-temperature-sterilized cow milk added with only TG (Control section 2) and the low-temperature-sterilized cow milk added with only "AROMILD U" (Control section 3), respectively.

After fermentation, each yogurt was left to stand at a low temperature (5° C.) and, 2 days later, its strength for fracture and the discharged or separated whey amount (weight ratio of the separated whey to the whole yogurt) were respectively measured.

The strength for fracture was measured by using a rheometer of FUDO KOUGYO K.K. The measurement conditions are as follows; a flat plate plunger having a diameter of 10 mm was used at a test rate of 6 cm/min. The amount of the discharged whey was measured as follows. A predetermined amount (30 g) of the yogurt was placed on filter paper (Whatman #1), the ratio of the amount of the filtrate obtained within a predetermined time (15 minutes) to the whole yogurt was determined, and the ratio was expressed as a value relative to Control section 1 (containing neither TG nor reducing agent) which was taken as 100%. Further, sensory evaluation was conducted by a panel of 10 trained panelists. The results are shown below in Tables 1 and 2.

TABLE 1

| | "AROMILD U" (%) | Amount of TG added (unit/g of Protein) | Reaction Time (h) | Strength for Fracture (g/cm²) | Discharged Whey Amount (%) |
|---|---|---|---|---|---|
| Control Section 1 | 0 | 0 | 4 | 9.8 | 100 |
| Control Section 2 | 0 | 2 | 4 | 10.8 | 98.1 |
| Control Section 3 | 0.02 | 0 | 4 | 10 | 100.3 |
| Test Section a (Inventive Product) | 0.02 | 2 | 1 | 24 | 76.3 |
| Test Section b (Inventive Product) | 0.02 | 2 | 2 | 40.7 | 70.8 |
| Test Section c (Inventive Product) | 0.02 | 2 | 4 | 48.1 | 67.9 |

TABLE 2

| | Comments | *Sensory Evaluation |
|---|---|---|
| Control Section 1 | Fragile, Large Amount of Separated Water | 2 |
| Control Section 2 | Soft, Large Amount of Separated Water | 2 |
| Control Section 3 | Soft, Large Amount of Separated Water | 2 |
| Test Section a | Small Amount of Separated Water, Very Smooth | 5 |
| Test Section b | Firm Texture | 3 |
| Test Section c | Firm Texture | 3 |

*Evaluation was made on a scale of 1 to 5.
1: poor,
2: rather poor,
3: ordinary,
4: rather good,
5: good As shown in Table 1, the breaking strength (i.e., the strength for fracture) of the section containing only TG (Control section 2) and the section containing only the reducing agent (Control section 3) were little different from that of the section containing neither TG nor reducing agent, (Control section 1), i.e., an improvement in the effect of improving the physical properties of the yogurts was not observed when only TG or only the reducing agent was added. As regards Test sections a to c (Inventive products, i.e., products according to the present invention), the breaking strength was increased with the passage of the reaction time of TG. Particularly, in the case of the Test section c, a firm gel was formed.

On the other hand, there was observed no distinct difference in the discharged whey amount among the Control sections 1 to 3. Apparently, they were liable to have separation of water such as separation of whey (i.e., syneresis), and the separation of water was glaring after they had been left to stand at room temperature for only 1 hour. As regards the Test sections a to c (Products according to the present invention), on the other hand, a significant difference was observed among the yogurts, and the discharged whey amount was decreased as the reaction time of TG was prolonged. It can be assumed that this is because water-holding capacty was improved by the modification of the raw material milk by TG. The results of the sensory evaluation revealed that, while the Control sections 1 to 3 were all given such unfavorable evaluations as "soft", "watery", "fragile", and the like, the products according to the present invention, particularly, the Test section a was given favorable evaluation as a yogurt which is very smooth, melts easily in the mouth and has little separation of water.

The Test section b was a so-called "hard-texture" yogurt, and its evaluation result was different between those who liked a hard texture and those who disliked a hard texture (in other words, the preferences of the panelists were greatly reflected on the evaluation result). However, it was not unpleasant on the tongue at all, and it was apparently a curd having little separation of water and a firm texture. As regards the Test section c, although the results of evaluating its physical properties such as strength for fracture and discharged whey amount were good, it exhibited rather hard mouthfeel as a yogurt as compared with the Test sections a and b. However, when it is considered that such a hard yogurt has heretofore been unable to be obtained by milk proteins only and the production of such a yogurt has to rely on some additives, the above facts suggest the possibility that a novel product form or mouthfeel of a yogurt can be provided.

As the effects expected from final products when the technology of the present invention is applied to yogurt, there may be mentioned, firstly, an increase in the viscosity of a stirring-type yogurt, an increase in the hardness of a still-type yogurt, impartment of favorable mouthfeel, improvements in physical properties regardless of decreased solid content, or decreased costs with the physical properties being maintained, and the like. Meanwhile, a still-type yogurt is liable to have separation of water when subjected to vibrations or other physical forces during distribution, whereby its commodity value may significantly lower. This problem can be solved by increasing the water holding ability (i.e., water-retainability) of a curd according to the present invention.

Recently, a variety of yogurts whose fats and saccharides are reduced in line with the consumers' interest in healthiness, are on the market, and it is known that these products often have impaired physical properties. However, when the technology of the present invention is employed, low-fat or low-calorie products can be provided while more favorable mouthfeel to consumers is maintained. Further, according to the present invention, a variety of thickening polysaccharides and other additives which have heretofore been used for improving the physical properties of a yogurt, have become dispensable, and more natural mouthfeel can be imparted to the yogurt.

Furthermore, for the purpose of stabilizing the quality of yogurts by improving the curd properties of yogurts or preventing the separation of water from yogurts, a heat treatment (whey protein-denaturing treatment) step has heretofore been required in the production process in addition to the above methods. This often serves also as the step of sterilizing raw materials, and the manufactures of yogurts are forced to select optimum conditions for the step.

One of the most excellent points of the present invention is that extra thermal energy can be saved since heat treatment is not required for the purposes other than sterilization. In addition, a reduction in the quality of a product by the excessive thermal denaturation of a milk protein, particularly whey, which is caused by the heat treatment, can be prevented, whereby the production of a dairy product such as a yogurt or the like which has a flavor closer to that of raw milk or makes good use of the flavor of raw milk can be facilitated.

The application of the present invention is not limited to yogurts since the present invention can be applied to all kinds of raw milks.

Next, a description will be given to the case where the technology of the present invention is applied to the production of powdered milk or cheeses.

Example 4

Production of Powdered Milk

An enzyme preparation of TG ("ACTIVA" TG, specific activity: 1,000 U/g of the preparation, product of AJINOMOTO CO., INC.) was added to 1 liter of low-fat low-temperature-sterilized cow milk (kept at 63° C. for 30 minutes to be sterilized; non-fat milk solid: 8.4%; content of protein: 3.1%; milk fat: 1.5%) in the proportion of 2 units per 1 gram of the milk proteins, and at the same time, "AROMILD U" (yeast extract containing 8% of glutathione) was added in the proportion of 0.02% based on the raw material milk. While maintained at 40° C., the mixture was stirred for reaction for 3 hours (2U product: product of the present invention). To terminate the reaction, the mixture was heated to 90° C. and then immediately cooled. This cow milk modified with the use of TG was then frozen at −40° C. Then, the frozen milk was freeze-dried in a vacuum to obtain powdered milk (Test product) from the product of the present invention.

On the other hand, for comparison's sake, powdered milks were prepared similarly from the low-fat low-temperature-sterilized cow milk added with neither TG nor reducing agent (Control section 1), the low-fat low-temperature-sterilized cow milk added with only the reducing agent (Control product 2) and the low-fat low-temperature-sterilized cow milk added with only TG (Control product 3). For further comparison's sake, powdered milk was prepared similarly from the low-fat low-temperature-sterilized cow milk added with only TG in an amount of 10 units per 1 gram of the milk proteins (Control product 4).

(Kinetic Analysis of Acidic Gelation by Dynamic Viscoelasticity Meter)

As a rheological technique for examining the process of gel formation, there can be used a method of tracking the change in elastic modulus with time at constant temperature and frequency (Dickinson et al., J. Agric. Food Chem. (1996), 44, 1371 to 1377). By using this method, the change with time in the storage elastic modulus (G') of the powdered milk obtained above (Test product) when a 15% (w/w) solution of the powdered milk was acidified, was monitored. Further, the Control products 1 to 4 were subjected to the same method. The apparatus used was "Stress Tech Rheometer DAR-100" (product of Seiko Denshi Kogyou K.K.).

Figure 4:
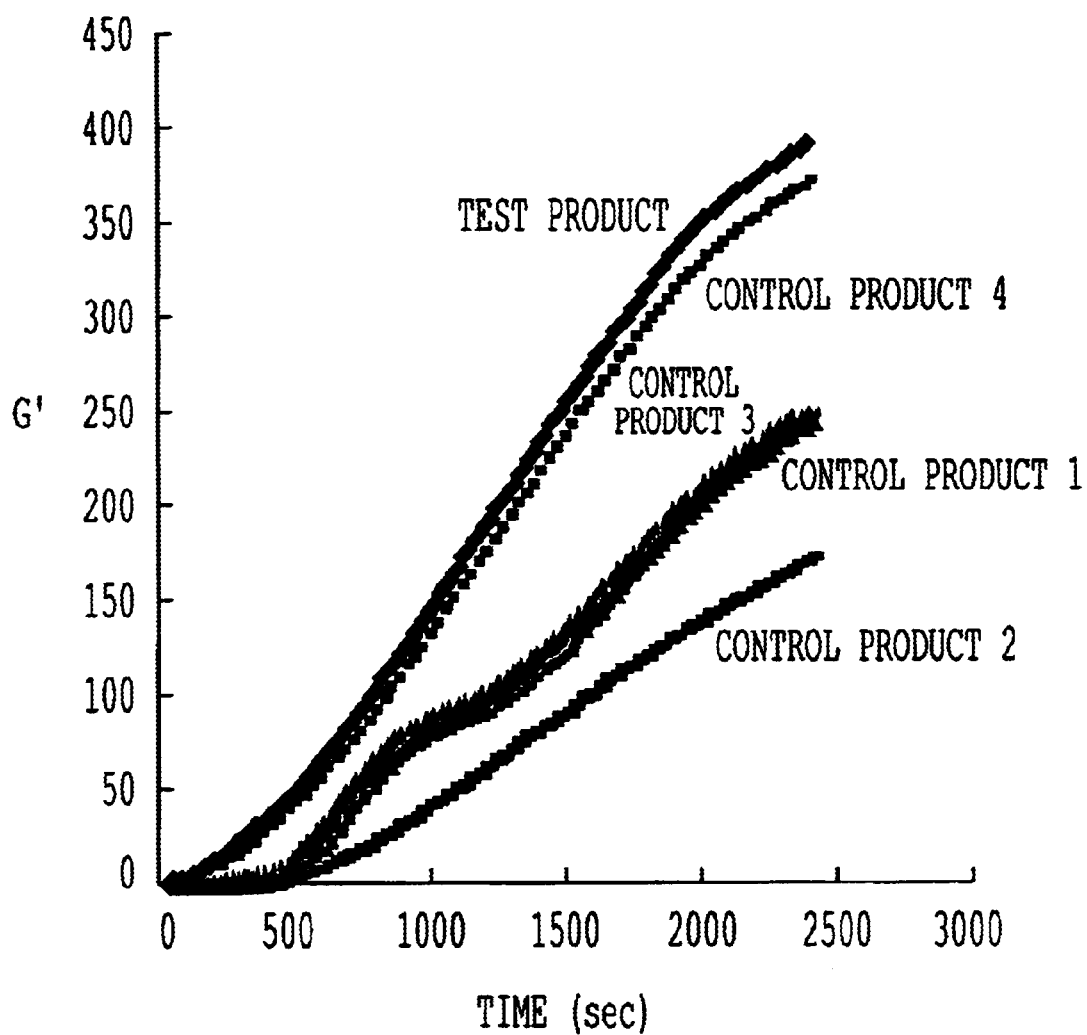
FIG. 4 shows a change in the storage elastic modulus (G') of TG-treated freeze-dried powdered milk.

The acidification of the powdered milk solution was started by the addition of 3.2% (w/w) glucono-δ-lactone, and while the sample was kept at 40° C., the change in storage elastic modulus (G') was monitored for 40 minutes (2,400 seconds). The results are shown in FIG. 4. The gelation of the Test product proceeded faster than the gelations of the Control products 1 to 3, and the viscosity of the gel became about 1.6 times after 40 minutes. As regards the Control products 2 and 3, the effect caused by the addition of only the reducing agent or only TG was hardly observed. Rather, as far as the addition of only TG (Control product 2) was concerned, the gelation slightly slowed down. Furthermore, for comparison's sake, as to the case (Control product 4) where TG was solely added in an amount of 10 units per 1 gram of the milk proteins, it exhibited similar gelation behavior although the gelation was slightly slow as compared with the Test product. Thus, it was shown that the amount of TG to be added could be decreased to about one-fifth of the conventional amount according to the present invention.

Thus, it can be expected that powdered milk having thus-improved acidic gel formability is used as a raw material for a variety of food products as well as dairy products. For example, powdered milk such as skimmed milk powder or the like is frequently used as a raw material in the yogurt production. In such a case, if powdered milk having a high gel formability is used, the use of the aforementioned additives for the improvement of the gel can be reduced. Further, if this powdered milk is used in the production process of a yogurt, no extra step for the reaction of TG needs to be provided and conventional production conditions do not need to be modified.

In general, powdered milk can be applied to a wide variety of food products, and the application value of the modified powdered milk thus-produced according to the present invention is not limited to the above-described production of a yogurt.

Whereas, a cheese is generally made from raw milk, and the raw material milk therefore is heat-treated for the sakes of hygiene and uniform quality. However, traditional cheeses such as "EMETAL" from Switzerland, "ROCK-FALL" from France, and "PALMIJANO" and "REJANO" from Italy are carefully made from raw milk of high quality in their birthplaces. The heat treatment is often carried out at 71 to 75° C. for up to 15 seconds (it may be too mild to be called sterilization). Excessive heating causes the non-ionization of calcium ions, denaturation of whey proteins, formation of soft curd, retardation of syneresis, and the like, whereby the quality of a cheese may be degraded and, in particular, a bitter taste is caused.

Since excessive heating is not desirable in the production of a cheese as described above, a technology of the present invention which can also be applied to raw milk is very promising from the viewpoint of an improvement not only in the physical properties of a cheese but also in the quality thereof.

Further, the advantages of using TG for a cheese include an increase in the yield of curd and improvements in flavor, taste, appearance and the like (Japanese Patent Application Laid-Open No. 134947/1995). In addition to these advantages, the present invention also brings about such merits that the amount of TG to be added or used can be decreased as compared with that used in the prior art, that the reaction time can be shorten, and the like.

A description will be given to an example in which the technology of the present invention is applied to the production of a cheddar cheese, this example being compared with another example in which TG is used in the production of the cheese in accordance with a conventional method (Japanese Patent Application Laid-Open No. 134947/1995). The conventional method is a method in which only TG is added to raw material milk.

Example 5

Production of Cheddar Cheese

11 Liters of low-temperature-sterilized cow milk (sterilized at 63° C. for 30 minutes; non-fat milk solid: 8.4%; milk fat: 3.6%; content of milk protein: 3.1%) was heated to 33° C. An enzyme preparation of TG ("ACTIVA" TG, specific activity: 1,000 U/g of the preparation, product of AJINOMOTO CO., INC.) was added to the milk in an amount of 1 unit per 1 gram of the milk proteins, and at the same time, "AROMILD U" was added in the proportion of 0.02% based on the weight of the raw material milk.

After 30 minutes, a lactic bacteria starter (mixture of *S. lactis* and *S. cremoris*, product of Chrischan Hansen's Laboratories) was added to the above mixture in the proportion of 0.75% based on the weight, and the resulting mixture was kept at 33° C. for 30 minutes. Then, 0.004% of calf rennet (single strength, product of Chrischan Hansen's Laboratories) and 0.02% of calcium chloride were added to the mixture. The resulting mixture was left to stand for 30 minutes, whereby a curd was formed. After this curd was cut and left to stand for 5 minutes, it was stirred slowly for 10 minutes and then heated to 34° C. While the curd was heated, it was kept stirred slowly without crushing curd grains. Then, the curd was stirred at 38° C. for 15 minutes. After left to stand for 5 to 10 minutes, the curd was allowed to discharge the separated whey.

After the discharge of the whey, the resulting curd was cut to 6-inch widths, and the cut pieces of the curd were piled up. Thereafter, while kept at 37 to 38° C., the piled-up curd was repeatedly reversed every 15 minutes, whereby it is encouraged to discharge the whey (cheddaring process). Then, the curd was milled. Salt (sodium chloride) was mixed into the milled curd little by little, i.e., the salt was divided into three portions and added in such amount that the concentration of the salt would be 4.5% of the curd. Thereafter, the resulting curd was filled in a container, compressed, aged and stored to be a cheddar cheese product (Test product).

For comparison's sake, a cheddar cheese (Control product) was produced in the same manner but except that neither TG nor AROMILD U was added, and a cheese (Conventional product) was prepared in the same manner but by the conventional method, that is, by adding 5 units of TG per 1 gram of the milk proteins.

The weights of the compressed curds and the dry weights thereof were measured, and sensory evaluation was made on the cheddar cheeses aged for three weeks by a panel of 10 trained panelists. The Test product, Control product and Conventional product were compared with one another, and the results of the comparison are shown below in Table 3.

TABLE 3

|  | Control Product | Test Product | Conventional Product |
| --- | --- | --- | --- |
| TG | — | 1 U/g of Protein | 5 U/g of Protein |
| "AROMILD U" (%) | — | 0.02% | — |
| Weight of Compressed Curd (g) | 887 | 1028 | 983 |
| Dry Weight of Curd (g) | 521 | 605 | 571 |
| Yield of Curd (%) (Control Product as 100%) | 100 | 116 | 109 |
| Cohesiveness of Cheese Block | Good | Good | Good |
| Physical Properties | Moderate Hardness | Moderate Hardness, Rather Elastic | Moderate Hardness |
| Mouthfeel | Smooth on Tongue | Smooth on Tongue | Smooth on Tongue |

As shown in Table 3, the curd yield of the Test product was increased from that of the Control product by about 15%. Further, its hardness was satisfactory, and its elasticity was increased as compared with the curd of the Control product. Its flavor and appearance were not so different from those of the Control product. On the other hand, the curd yield of the Conventional product was slightly lower than but almost the same as that of the Test product. Further, the hardness, appearance and results of the sensory evaluation of the Conventional product were almost the same as those of the Test product. It can be understood from the foregoing that the amount of TG used in the conventional method in which only TG was added, could be reduced to about one-fifth according to the present invention.

A cheddar cheese is a so-called "hard cheese" (water content: about 40% or lower). It is produced in the largest quantity in the world and also used as a raw material for a processed cheese. Its mild flavor tends to conform to the preferences of many people easily.

The present invention which can reduce the conventional amount of TG, increase the yield of curd, and provide curd having good hardness and elasticity and, in turn, a hard cheese of high quality such as a cheddar cheese or the like, is extremely useful from the industrial standpoint.

[Effects of the Invention]

According to the technology of the present invention, by adding TG and a reducing agent to raw material milk such as raw milk which has low reactivity to TG and causing them to react with the raw material milk, the reactivity of the raw material milk can be increased, and milk proteins can be modified more effectively than before. Furthermore, according to the technology of the present invention, the required amount of the reducing agent is at such level where it can be added to food products and therefore, the practicality of the reducing agent is high. Therefore, it can be widely applied to improving the physical properties of a dairy product using raw milk such as a yogurt.

We claim:

1. A method of preparing a dairy product, comprising modifying a raw material milk by causing transglutaminase to act on said raw material milk, wherein a reducing agent is added to said raw material milk when said transglutaminase is caused to act on said raw material milk.

2. The method of claim 1, wherein said raw material milk is selected from the group consisting of raw milk, skimmed milk, partially skimmed milk, and processed milks thereof.

3. The method of claim 1, wherein said raw material milk is a casein-containing solution obtained by processing a raw material milk selected from the group consisting of raw milk, skimmed milk, partially skimmed milk, and processed milks thereof.

4. The method of claim 1, wherein said reducing agent is at least one compound selected from the group consisting of reduced glutathione, cysteine, γ-glutamylcysteine, sulfurous acid, ascorbic acid, erythorbic acid, salts thereof, and preparations containing at least one of these reducing agents.

5. The method of claim 1, wherein said reducing agent is added in an amount of $1 \times 10^{-5}$ to $1 \times 10^{-1}$ g per 1 gram of non-fat milk solid, present in said raw material milk.

6. The method of claim 1, wherein said transglutaminase is caused to act upon the raw material milk in an amount of 0.001 to 20 units per 1 gram of milk protein, present in said raw material milk.

7. The method of claim 1, wherein said raw material milk is selected from the group consisting of raw milk, skimmed milk, partially skimmed milk, and processed milks thereof, and wherein said reducing agent is at least one compound selected from the group consisting of reduced glutathione, cysteine, γ-glutamylcysteine, sulfurous acid, ascorbic acid, erythorbic acid, salts thereof, and preparations containing at least one of these reducing agents.

8. The method of claim 7, wherein said reducing agent is added in an amount of $1 \times 10^{-5}$ to $1 \times 10^{-1}$ g per 1 gram of non-fat milk solid, present in said raw material milk.

9. The method of claim 8, wherein said transglutaminase is caused to act upon the raw material milk in an amount of 0.001 to 20 units per 1 grain of milk protein, present in said raw material milk.

10. The method of claim 7, wherein said transglutaminase is caused to act upon the raw material milk in an amount of 0.001 to 20 units per 1 gram of milk protein, present in said raw material milk.

* * * * *